United States Patent [19]

Mouser et al.

[11] Patent Number: 4,873,648

[45] Date of Patent: Oct. 10, 1989

[54] WATERCUT MONITOR DEVICE AND METHOD

[75] Inventors: Charles L. Mouser; Joseph A. Stewart, both of Duncan, Okla.

[73] Assignee: Halliburton Company, Duncan, Okla.

[21] Appl. No.: 45,974

[22] Filed: Apr. 30, 1987

[51] Int. Cl.$^4$ .............................................. G01F 1/00
[52] U.S. Cl. ................................. 364/500; 364/510; 73/61.1 R; 73/861.04
[58] Field of Search ............ 364/497, 500, 509, 510, 364/551; 73/61.1 R, 861.04, 861.14

[56] References Cited

U.S. PATENT DOCUMENTS

| | | | |
|---|---|---|---|
| 3,906,198 | 9/1975 | November | 364/510 |
| 4,055,082 | 10/1977 | November | 364/510 |
| 4,059,744 | 11/1977 | Elderton | 364/510 |
| 4,090,408 | 5/1978 | Hedrick | 364/509 |
| 4,340,938 | 7/1982 | Rosso | 364/510 |
| 4,416,153 | 11/1983 | Williams | 364/509 |
| 4,470,300 | 9/1984 | Kobayashi | 73/61.1 R |
| 4,502,126 | 2/1985 | Mizoguchi | 364/509 |
| 4,689,989 | 9/1987 | Aslesen et al. | 73/61.1 R |

Primary Examiner—Parshotam S. Lall
Assistant Examiner—Ellis B. Ramirez
Attorney, Agent, or Firm—James R. Duzan; E. Harrison Gilbert, III

[57] ABSTRACT

A watercut monitor device has an oscillator circuit which generates an analog input signal in response to the capacitance of a capacitance probe through which an oil and water emulsion flows. The frequency of the analog input signal is non-linearly related to the watercut of the emulsion. The analog input signal is effectively gated through a digital gating circuit, and a count related to the frequency of the gated signal is digitally made. The digital count addresses a digital memory having digital values, which are linearly related to the watercut of the emulsion, stored therein. Upon being addressed, the digital memory outputs the digital value stored in the addressed location. The digital value is optically coupled to a digital-to-analog converter which converts the digital value into an analog output signal linearly related to the watercut of the emulsion.

20 Claims, 7 Drawing Sheets

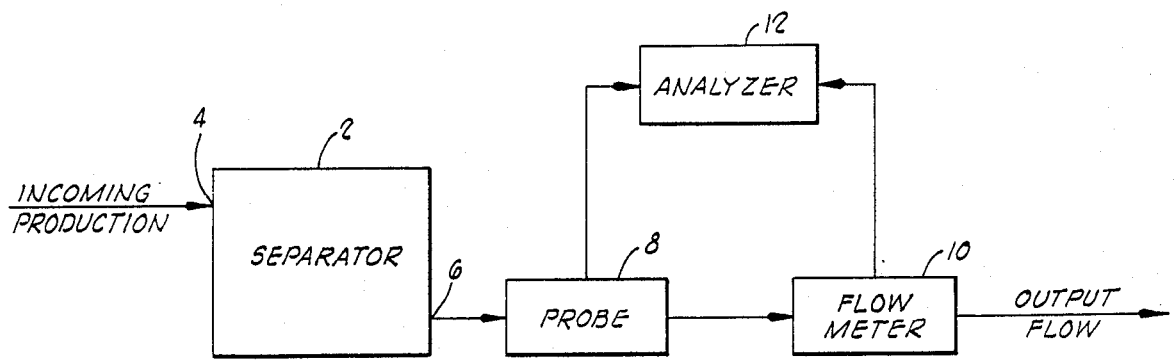
FIG. 1
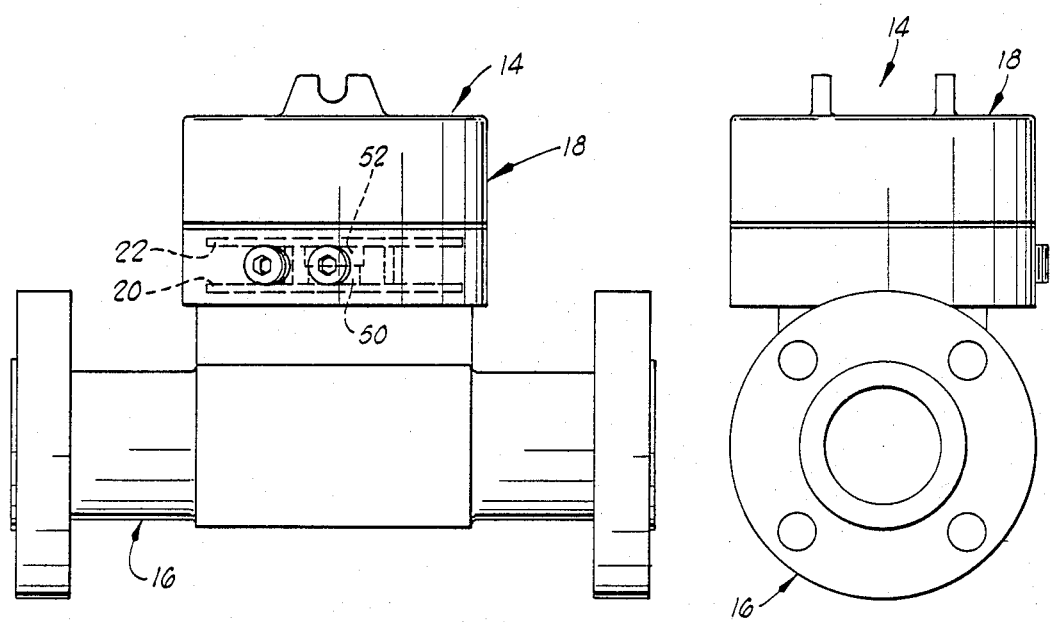 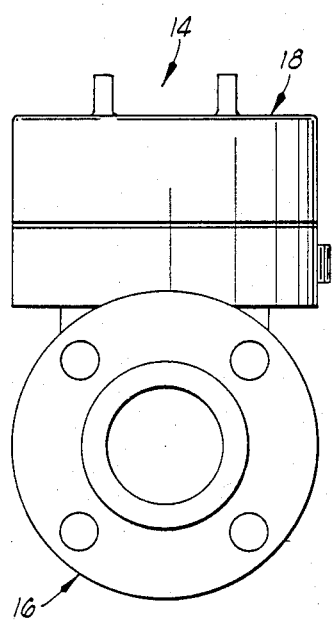
FIG. 2  FIG. 3

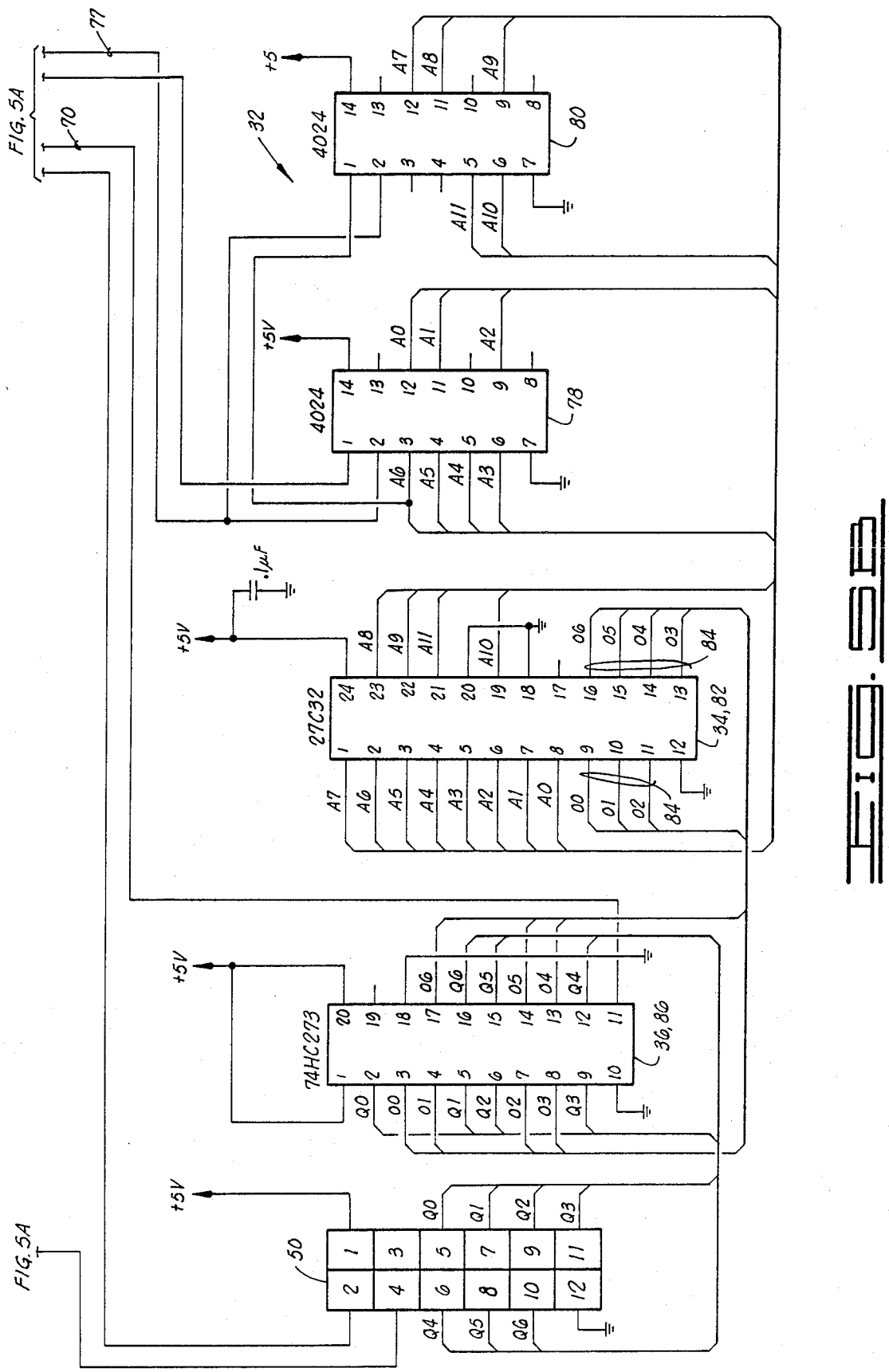

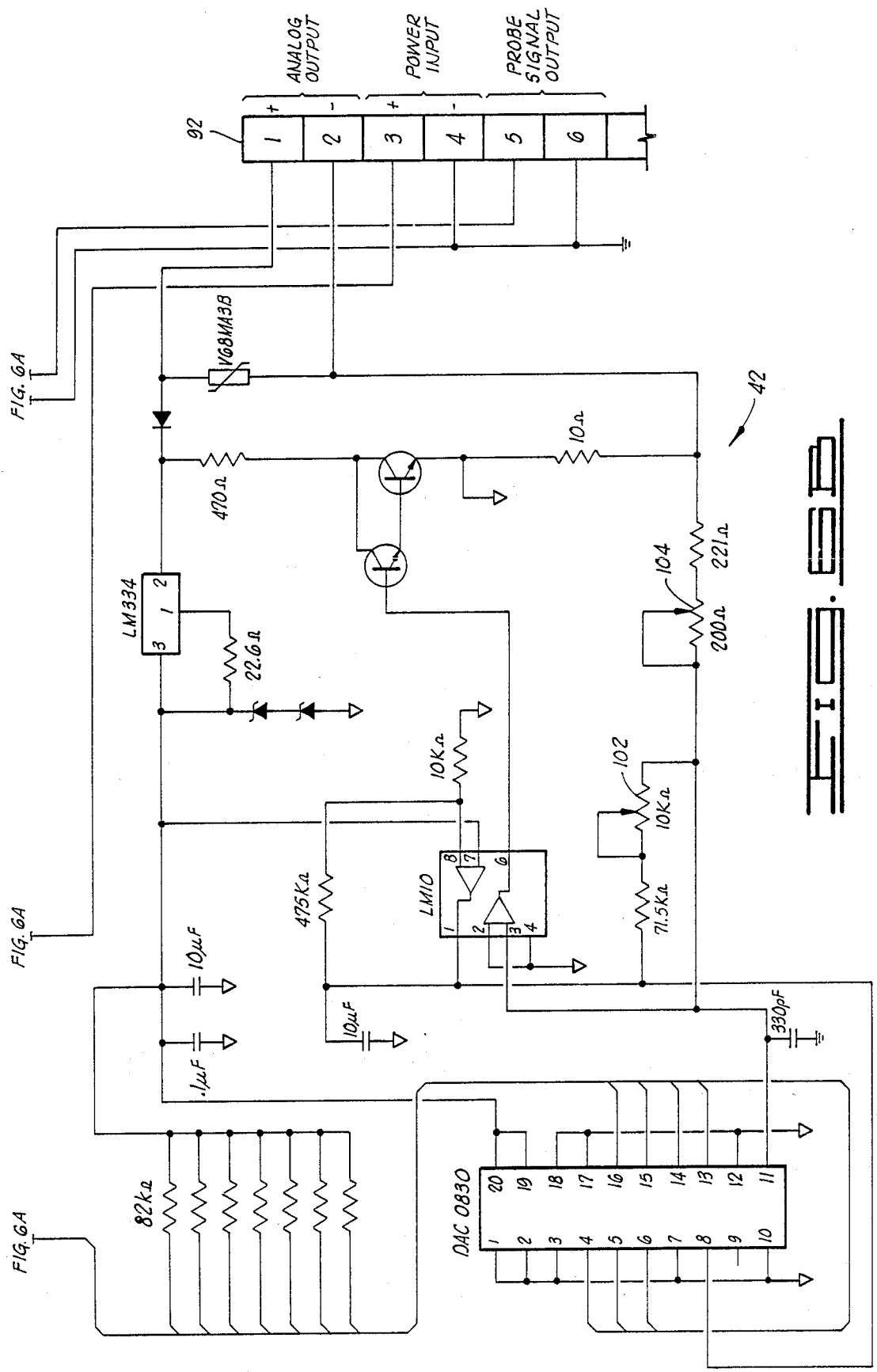

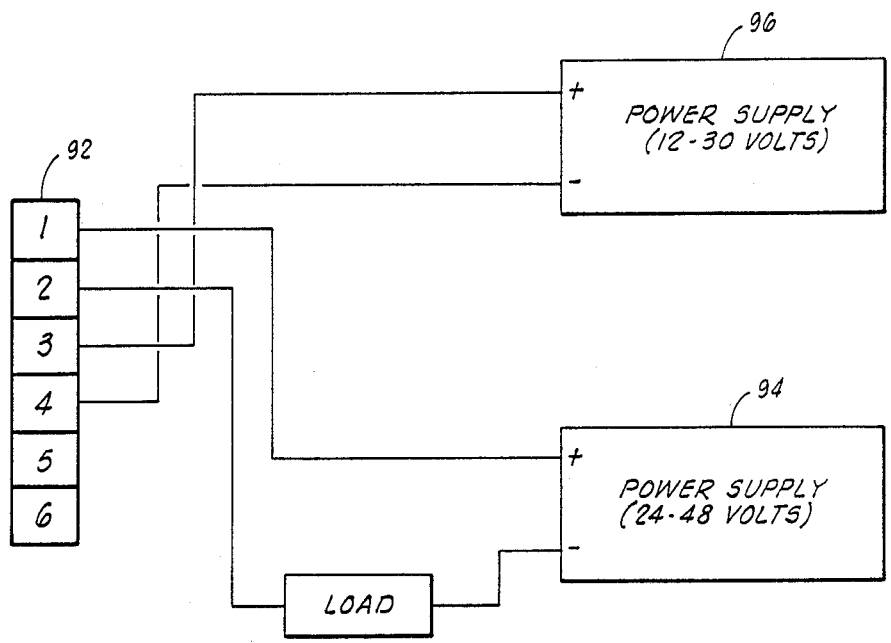
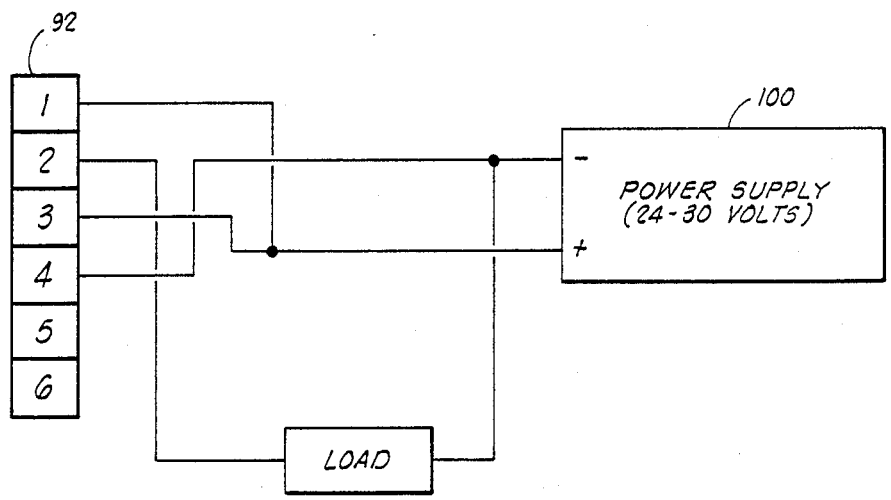
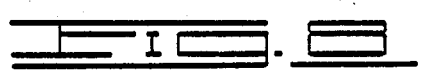

WATERCUT MONITOR DEVICE AND METHOD

BACKGROUND OF THE INVENTION

This invention relates generally to apparatus and methods for providing a linearized analog signal proportional to the watercut of an emulsion and more particularly, but not by way of limitation, to such a device and method utilizing a programmable read only memory containing digital values which effectively linearize the non-linear response of a capacitance probe to the percent of water in the monitored emulsion.

The liquid produced from an oil well is an emulsion when the liquid includes both oil and water, which is the case for production obtained from a well produced by a water flood operation, for example. Some of the water may be separated from the emulsion by flowing the emulsion through a separator; however, the stream from the outlet of the separator is generally still an emulsion because it has some water mixed with the oil. To determine how much water remains—which is desirable information to have because it enables one to determine whether further separation should be performed, for example—a watercut (percentage of water) measurement is made.

A general technique known to us for making a watercut measurement uses a capacitance probe yielding an electrical capacitance non-linearly variable in response to changes in the percentage of water in the emulsion. The technique of measuring the watercut with a capacitance probe is well known. See, for example, *Journal of Petroleum Technology*, November, 1962, "BS&W Measurements Principles and Practices", W. J. Warren and *Journal of Petroleum Technoloqy*, October, 1968, "Digital Instrumentation for Net Oil Measurement in Well Testing", Carl W. Zimmerman et al. This technique using a capacitance probe allows one to determine the proportions of an oil-water flow without requiring the actual physical separation of the two liquids.

Equipment for making a watercut measurement with a capacitance probe is or has been made or offered by companies including Halliburton Services (a division of Halliburton Company), Hydril Company, Baker Production Services, C. E. Invalco, General Manufacturing Company, and Engelman-General, Inc. This equipment typically provides a signal from a watercut monitor device which includes the capacitance probe; it also provides a signal from a flow meter; these two signals are provided to a computer or analysis device located in a housing separate from the watercut monitor device and the flow meter; the housing has displays visually showing the watercut and the totals of oil and water computed on the basis of the information derived from the signals from the watercut monitor and the flow meter. One or more of the watercut monitor devices are believed to use operational amplifiers and filter circuits to provide a linear analog output. One or more are believed to use frequency-to-voltage conversion or analog integration techniques to compensate for the non-linear responses of the capacitance probe; in at least one of these types of equipment, linearization is done in the readout device under microprocessor control using a look-up table of linearized values. Such analog circuits require retrimming or redesign to accommodate changes in the linearization or in the characteristic of the output signal from the watercut monitors (e.g., does full-scale output indicate 100% watercut or something less). As to at least the digital linearization performed under microprocessor control, this is done in a different unit from the watercut monitor device. In general, these types of equipment have been provided as complete systems to be used intact by customers.

Increasingly, however, there has been a demand in the oilfield for instrumentation which will enable the information derived from the primary sensor, such as the watercut monitor including the capacitance probe, to be provided as an analog signal having a desired characteristic linearly related to the detected watercut so that such signal can be transmitted directly to a central computing device, thereby obviating the need for the intermediate analysis and readout devices which have heretofore been used. Therefore, there is the need for an improved watercut monitor device and method which linearize the non-linear capacitance probe output by strictly digital techniques to facilitate maintenance and modification, but which ultimately provide a linearized analog signal as an output for use by other equipment. Such improved device and method would enable users to have a compatible linear analog signal for use in their own analysis equipment.

SUMMARY OF THE INVENTION

The present invention overcomes the above-noted and other shortcomings of the prior art and meets the aforementioned needs by providing a novel and improved watercut monitor device and method. The invention uses digital techniques to linearize non-linear analog signals derived from a capacitance probe. The invention then converts the digital response to an analog signal linearly related to the percentage of water in the monitored emulsion.

The apparatus of the present invention for providing an analog output signal which is linearly proportional to the percentage of water in an emulsion comprises: analog input means for generating an analog input signal non-linearly proportional to the percentage of water in the emulsion; digital means, responsive to the analog input means, for digitizing the analog input signal and for translating the digitized analog input signal into a digital signal linearly proportional to the percentage of water in the emulsion; and analog output means, responsive to the digital means, for converting the digital signal into an analog output signal so that the analog output signal is also linearly proportional to the percentage of water in the emulsion.

The method of the present invention comprises the steps of: (a) generating a cyclic electrical signal having its cyclic period non-linearly responsive to the watercut; (b) counting the number of cyclic periods of the electrical signal occurring during a predetermined time; (c) communicating the count obtained in step (b) to address lines of an integrated circuit digital memory including memory locations at which digital values are stored, each digital value defining a linearization of a count of the number of cyclic periods of the electrical signal; (d) outputting from the digital memory, in response to step (c), the digital value stored at the memory location addressed by the communicated count; and (e) converting the digital value output in step (d) into an analog signal having a detectable characteristic representing the linearization defined by the output digital value.

Therefore, from the foregoing, it is a general object of the present invention to provide a novel and improved watercut monitor device and method. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 1 is a block diagram illustrating an environment in which the present invention is contemplated to be used.

FIG. 2 is a side elevational view of a support body of the watercut monitor device of the preferred embodiment of the present invention.

FIG. 3 is an end elevational view of the support body shown in FIG. 2.

FIGS. 5A and 5B are schematic circuit diagrams of the preferred embodiment of the oscillator, signal conditioning, gating, counter, programmable read only memory, latch, and crystal oscillator and divider circuit components shown in FIG. 4.

FIGS. 6A and 6B are schematic circuit diagrams of the preferred embodiment of the drivers and opto-isolators and the digital-to-analog circuit components shown in FIG. 4.

FIG. 7 is a block diagram illustrating power supply connections for a two-power supply operation of the embodiment shown in FIGS. 5 and 6.

FIG. 8 is a bloc digram illustrating power supply connections for a one-power supply operation of the embodiment shown in FIGS. 5 and 6.

DETAILED DESCRIPTION OF THE PREFERRED EMBODIMENT

Figure 4:
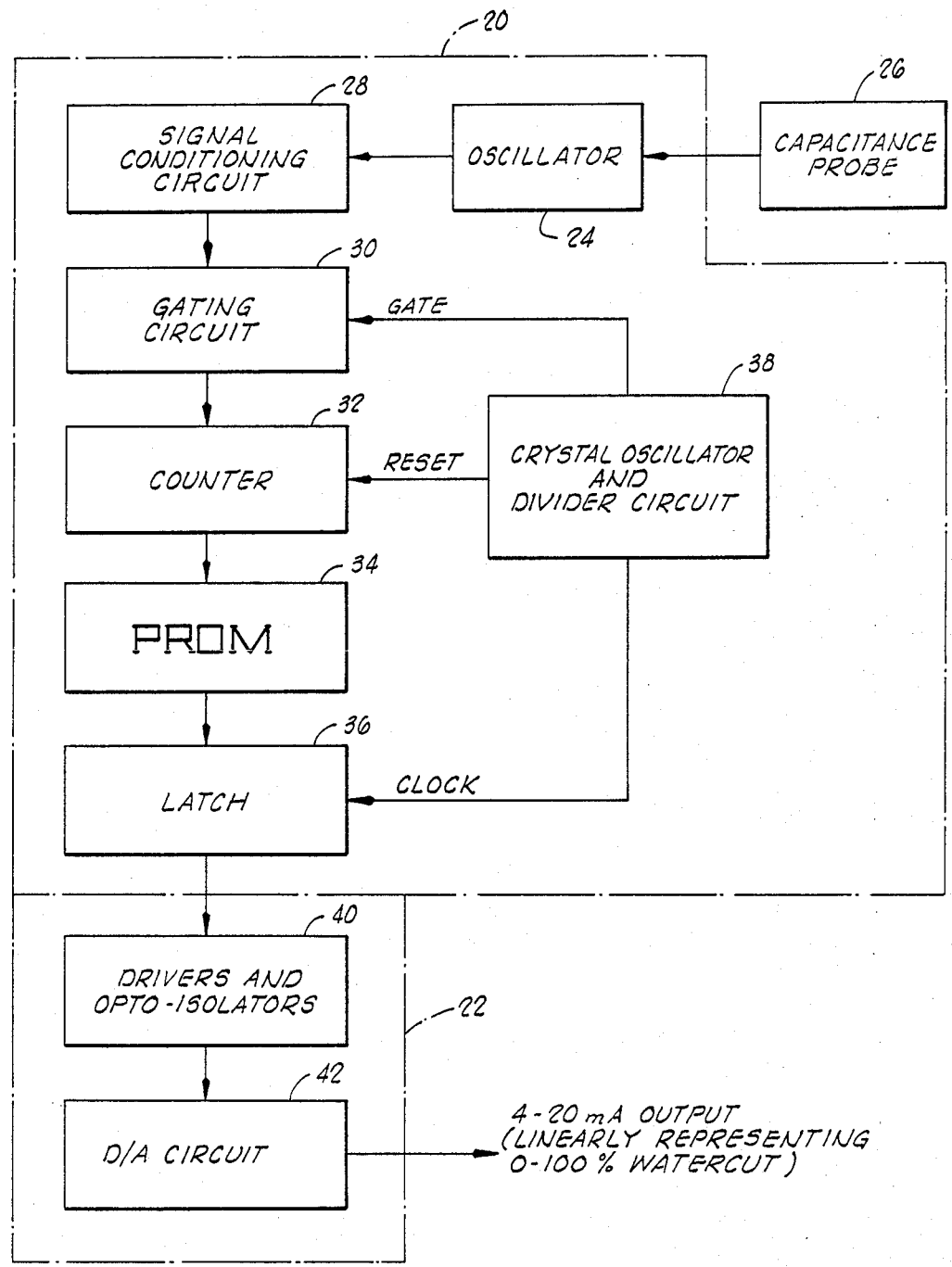
FIG. 4 is a block diagram of the operational components of the preferred embodiment of the watercut monitor device of the present invention, which components are disposed within the support body shown in FIGS. 2 and 3.

Shown in FIG. 1 is an arrangement which is known in the art for determining the watercut and the totals of oil and water of an oil-water emulsion. This arrangement includes a separator 2 having an inlet 4 which receives an incoming production stream from a producing oil well. The separator 2 includes an outlet 6 from which flows an emulsion having a reduced watercut due to the separation of some of the water from the inlet production stream which occurs within the separator 2 in a manner as known to the art.

A watercut monitor device 8 and a flow meter 10 are connected in series in the conduit through which flows the reduced watercut emulsion exiting the outlet 6. The monitor 8 and the flow meter 10 provide respective signals to an analyzer device 12. Heretofore, the monitor 8, the flow meter 10 and the analyzer 12 have usually been provided as an integrated system with the analyzer 12 displaying the calculated watercut (determined in response to the probe 8 signal) and the calculated total water and oil (determined in response to the probe 8 signal and the flow meter 10 signal). An example of such a system is the Net Oil Analyzer of Halliburton Services.

The arrangement shown in FIG. 1 defines the same environment in which the present invention is contemplated to be used; however, the present invention provides a new and improved type of watercut monitor 8. That is, the monitor 8 of the present invention is made to yield a linearized analog output signal capable of use with other equipment to which the output signal is compatible as desired by the end user.

Because the separator 2, the flow meter 10 and the analyzer 12 do not form parts of the present invention, only the new and improved watercut monitor 8 will be further described.

As shown in FIGS. 2 and 3, the water cut monitor device 8 of the present invention has a support body 14 of a type as known to the art. The support body 14 of the preferred embodiment is specifically of the type used for the Halliburton Services Net Oil Analyzer. This structure includes a flow tube 16 (having suitably connectible ends, such as the illustrated flanges) in which a capacitance probe (not shown in FIGS. 2 and 3) is disposed in a manner known to the art. The flow tube 16 is inserted in line with the flow line or conduit extending from the outlet 6 of the separator 2 for the environment shown in FIG. 1. Extending perpendicularly from, but connected to, the flow tube 16 is a housing 18 in which the electronic components of the present invention are disposed. The electronics (except for the capacitance probe which is associated with its own printed circuit board as known to the art) are mounted on two printed circuit boards 20, 22 mounted axially within a hollow cavity of the housing 18 as shown in phantom in FIG. 2. The circuits are electrically connected to the capacitance probe in a manner as known to the art.

The lower board 20 (i.e., the one closer to the capacitance probe and the flow tube 16) is installed within the housing 18 so that two banana plugs on the circuit board 20 are inserted into mating jacks in the circuit card housing of the capacitance probe in a manner as known to the art. A screw is installed in a center hole of the circuit card 20 to secure it to the support body 14. This holds the circuit card 20 in the housing 18 and connects the circuit card 20 to the capacitance probe.

The upper circuit board 22 is installed so that connecting pins on the bottom of the upper board 22 are inserted into mating sockets on the lower board 20. The upper board 22 is attached to the lower board 20 by threading two screws through holes in the board 22 and into standoffs of the lower board 20. This secures the upper board 22 in the housing 18 and electrically connects it to the circuits of the lower circuit board 20.

As illustrated in FIG. 4, the components of the water cut monitor device 8 mounted on the lower circuit board 20 include an oscillator circuit 24 having an input connected to the capacitance probe (identified by the reference numeral 26 in FIG. 4) and having an output connected to an input of a signal conditioning circuit 28. The signal conditioning circuit 28, which is also mounted on the circuit board 20, has an output connected to an input of a gating circuit 30 in turn having an output connected to a counter circuit 32 which provides outputs to inputs of a programmable read only memory (PROM) 34. The outputs of the PROM 34 are connected to inputs of a latch 36. Elements 30, 32, 34, 36 are also mounted on the printed circuit board 20. A crystal oscillator and divider circuit 38, providing outputs to the gating circuit 30, the counter 32 and the latch 36, is mounted on the printed circuit board 20.

The outputs from the latch 36 are connected to inputs of driver and opto-isolator circuits 40 having outputs connected to inputs of a digital-to-analog circuit 42. The components 40, 42 are mounted on the upper printed circuit board 22 as indicated in FIG. 4.

In the preferred embodiment the capacitance probe 26 and the oscillator circuit 24 define analog input means for generating an analog input signal which is non-linearly proportional to the percentage of water in the emulsion flowing through the flow tube 16 of the present invention. The components 28, 30, 32, 34, 36, 38 define in the preferred embodiment digital means, responsive to the analog input means, for digitizing the analog input signal and for translating the digitized analog input signal into a digital signal linearly proportional to the percentage of water in the emulsion. The driver and opto-isolator circuit 40 and the digital-to-analog circuit 42 define in the preferred embodiment analog output means, responsive to the digital means, for converting the digital signal into an analog output signal so that the analog output signal is also linearly proportional to the percentage of water in the emulsion. Therefore, in between the analog input and analog output stages of the water cut monitor device 8 of the present invention, there is implemented a strictly digital linearization technique by which the water cut monitor 8, by itself, ultimately generates an analog output signal linearly proportional to the watercut of the emulsion acting on the capacitance probe 26.

The capacitance probe 26 is any suitable type known to the art. For example, the capacitance probe can be the same one as used in the Halliburton Services Net Oil Analyzer. As previously described, the capacitance probe 26 is mounted in the flow tube 16 of the support body 14 in a manner as known to the art. It should be installed to provide easy access to the circuit board housing in order to facilitate calibration and maintenance. To operate properly in the preferred embodiment, the capacitance probe is to be installed vertically with either end up.

When an emulsion flows through the flow tube 16, the capacitance probe responds, in the form of electrical capacitance, to the percentage of water in the emulsion. This electrical capacitance is variable in response to changes in the percentage of water in the emulsion. This responsiveness is non-linear as known to the art. Also known to the art would be the particular non-linear relationship for any particular capacitance probe which may be used.

Figure 5A:
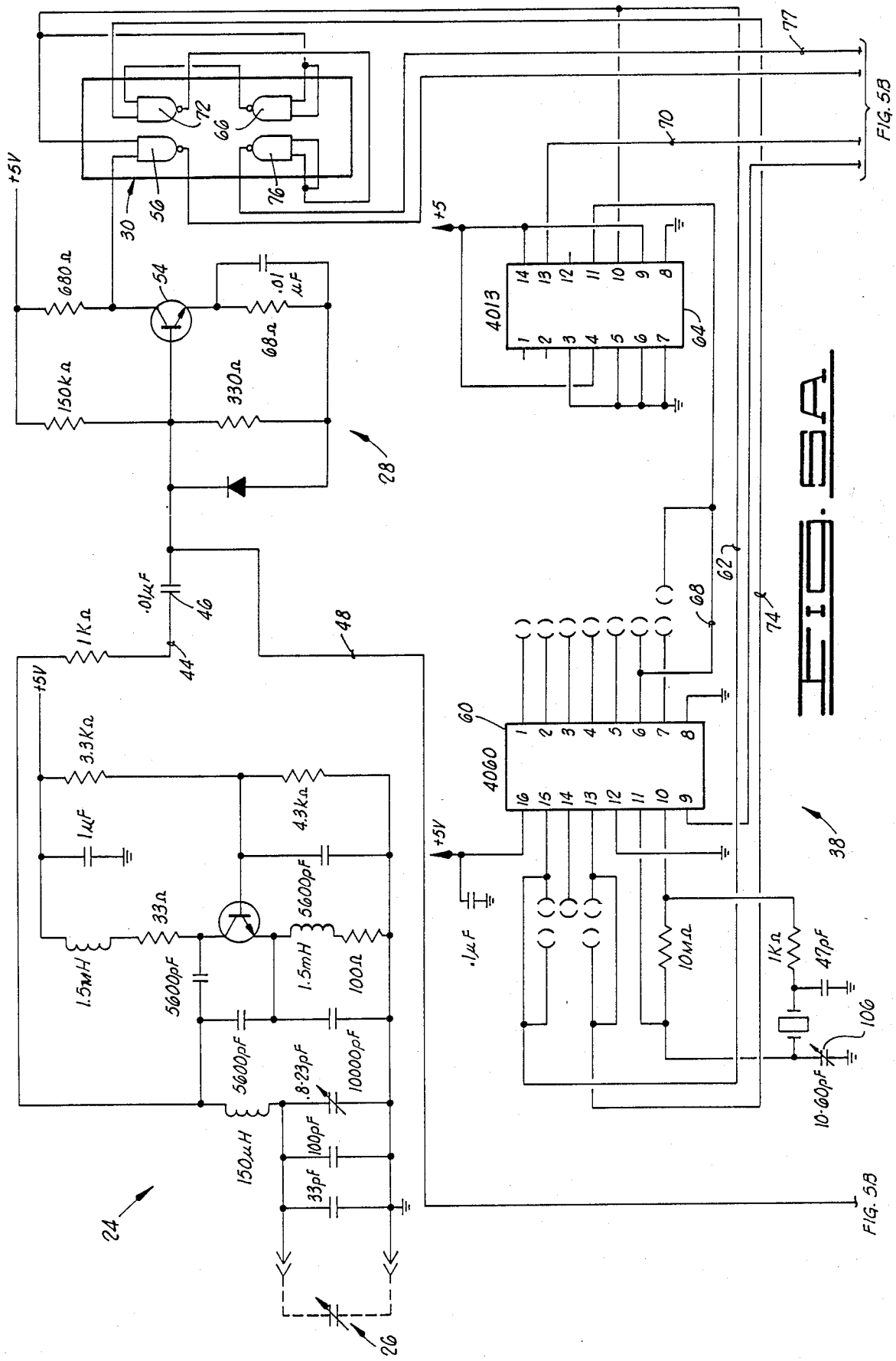

With reference to FIGS. 5A and 5B, the preferred embodiment of the elements 28, 30, 32, 34, 36, 38 contained on the lower printed circuit card 20 will be described.

The oscillator circuit 24 provides at its output an analog input signal which has a characteristic determined in response to the electrical capacitance of the capacitance probe 26. In the preferred embodiment the analog signal is an oscillating signal (specifically, a signal of sine waveform) having a frequency determined in response to the capacitance. Thus, the analog input signal of the preferred embodiment is a cyclic electrical signal whose period or frequency is responsive to the watercut of the monitored emulsion. The correlation between this characteristic of the analog input signal provided at the output of the oscillator circuit 24 is non-linear relative to the detected watercut.

In the preferred embodiment the circuit shown in FIG. 5A for implementing the oscillator circuit 24 is of a type as known to the art, specifically a Clapp oscillator which is the same type found in the Halliburton Services Net Oil Analyzer. The output from the oscillator circuit 24 is provided along a conductor 44 in which a capacitor 46 is serially connected to AC-couple the oscillating signal to the signal conditioning circuit 28. This signal is also connected, by a conductor 48, to a terminal member 50 (FIG. 5B). It is this member 50 which mechanically and electrically connects with a corresponding terminal member 52 (FIG. 6A) mounted on the upper circuit board 22 as shown in FIG. 2.

The signal conditioning circuit 28 interfaces the oscillating signal coupled through the capacitor 46 to the input of the gating circuit 30. This interfacing is implemented through a one-stage amplifier including a transistor 54. Through the transistor 54, the level of the oscillating signal from the oscillator circuit 24 is shifted and the waveform is shaped into a pulse waveform to make the oscillating signal compatible to the input of the integrated circuit embodiment of the gating circuit 30.

The gating circuit 30 forms part of a conversion means for periodically converting the analog input signal (in the form in which it is received from the signal conditioning circuit 28 in the preferred embodiment) into a respective digital count. The other elements of this conversion means in the preferred embodiment are the crystal oscillator and divider circuit 38 and the counter circuit 32.

The gating circuit 30 passes or blocks the interfaced analog input signal to or from the counter circuit 32 in response to the state of a gate control signal generated by the crystal oscillator and divider circuit 38. In the preferred embodiment, the gating circuit 30 communicates the number of cycles of frequency of the oscillating analog input signal in response to one of two states of the gate control, or timing, signal from the circuit 38. In response to a second state of this signal from the circuit 38, the gating circuit 30 does not communicate the number of cycles of frequency of the oscillating signal through to the counter 32.

In the preferred embodiment shown in FIG. 5A, the gating circuit 30 is implemented by a logic circuit 56 (specifically a NAND gate) comprising an input connected to the oscillator circuit 24 through the signal conditioning circuit 28. The logic circuit also comprises an input connected to the circuit 38, and it further comprises an output connected to the counter 32.

As mentioned, the gate control or timing signal controlling the operation of the NAND gate 56 is provided by the crystal oscillator and divider circuit 38. The circuit 38 may be defined as a clock or timing means for providing such a signal. This circuit further includes means for providing a counter reset signal to reset the counter 32 to zero at an appropriate time; it also includes means for providing a latch control signal to control he clocking or latching of the latch 36. In the preferred embodiment, the gate control signal actuates ("opens") the NAND gate 56 during a high logic state and it de-activates ("closes") the NAND gate 56 during a low logic state. To allow for propagation time and thereby to insure proper settling of data to be latched in the latch 36, the circuit 38 is designed in the preferred embodiment so that the latch control signal is generated during the low logic state of the gate control signal and so that the counter reset signal is generated after the latch control signal and before the next high logic state of the gate control signal.

These signals and this operation of the circuit 38 are obtained in the preferred embodiment by the components shown in FIG. 5A. The circuit 38 includes a crystal oscillator 58 providing a stable timing signal having a suitable frequency (32,768 hertz in the preferred embodiment). This signal drives an integrated circuit divider chip 60 having ten timing signal outputs. The gate control signal is provided from the divider 60 along a conductor 62. This signal is connected not only to the input of the NAND gate 56 as shown in FIG. 5A, but also to a reset input of a flip-flop circuit contained in an integrated circuit 64. The gate control signal is also communicated to the inputs of a NAND gate 66.

The latch control signal is provided through the flip-flop on the integrated circuit 64 when the gate control signal enables the flip-flop (via the reset input) and when the signal from the divider 60 communicated over a conductor 68 clocks the flip-flop. This generates the latch control signal which is communicated to the latch circuit 36 over a conductor 70.

The counter reset signal is generated in response to the gate control signal as applied through the NAND gate 66 to an input of a NAND gate 72 combined with a signal from the divider 60 provided to the other input of the NAND gate 72 over a conductor 74. The output of the NAND gate 72 is inverted through a NAND gate 76 whose output is connected through a conductor 77 to the reset inputs of the counter circuit 32 shown in FIG. 5B.

The counter circuit 32 is a digital counter which counts the pulses from the output of the NAND gate 56 corresponding to the cycles of the analog input signal passed through the NAND gate 56 when the gate control signal of the circuit 38 is in a high logic level state for the preferred embodiment shown in FIG. 5. The digital counter of the preferred embodiment is implemented by two serially connected integrated circuit counter chips 78, 80. Twelve of the available count outputs from this combination of integrated circuit chips are used to provide a twelve-bit count which is a binary representation of the number of cycles or periods of the analog input signal passed through the gate 56 for the respective gate period. The twelve bits of the count are connected to the twelve address inputs of a 4K-byte (i.e., 4,096 8-bit storage units or locations) programmable read only memory (PROM) 82 corresponding to the PROM 34 shown in FIG. 4.

The PROM 82 (34) and the latch circuit 36 define in the preferred embodiment another conversion means, this one for converting each respective digital count received from the counter circuit 32 into a respective digital value defining the ultimate digital signal to be output by the digital means into the analog output means of the present invention. The digital value is the means by which the linearization is achieved in the present invention as will be more particularly described hereinbelow.

The PROM 82 is the preferred embodiment of a digital memory which is used for storing each respective digital value at a memory storage cell or location (an 8-bit one in the preferred embodiment) having an address corresponding to a respective digital count from the counter circuit 32. Such a memory also includes the address inputs to which the digital counter count outputs are connected so that a digital count from the counter circuit 32 selects a respective memory storage location to retrieve the digital value stored at the selected location. Such a memory further includes data outputs to which a retrieved digital value is provided for communication to the latch circuit 36.

Although the memory embodied by the PROM 82 in the preferred embodiment provides an eight-bit output, only the least significant seven bits are used. The data outputs communicating these seven bits are collectively identified by the reference numeral 84 in FIG. 5B. Thus, when a digital count, defining a memory location address, is received at the address inputs of the digital memory, the respective digital value stored at the addressed location is output through the data outputs of the memory (with only the least significant seven bits being used for the implementation shown in FIG. 5).

The digital values which are stored in the digital memory are determined based upon the characteristics of the particular capacitance probe used and the resulting analog input signal provided therefrom and also based on the desired linearization and the nature of the output wanted. As to the consideration concerning the desired output, this refers to whether the full-scale output is to be scaled up to a 100% watercut or something less, for example. As to the considerations of the nature of the specific capacitance probe, resultant analog input signal and linearization, this is a matter of computation. That is, the frequency at each percent watercut for a particular capacitance probe would be known so that through mathematical operations one can directly convert to the desired linearity values for storage in the digital memory. By way of example, reference will be made to the following Table I:

TABLE I

| Probe Frequency (kHz) | % Water | Count (Pulses/Gate Period) |
|---|---|---|
| 835.929 | 99.5 | 773 |
| 837.008 | 98.5 | 790 |
| 838.12 | 97.5 | 807 |
| 839.259 | 96.5 | 825 |
| 840.42 | 95.5 | 843 |
| 841.62 | 94.5 | 862 |
| 842.84 | 93.5 | 881 |
| 844.089 | 92.5 | 900 |
| 845.369 | 91.5 | 920 |
| 846.68 | 90.5 | 941 |
| 848.02 | 89.5 | 962 |
| 849.38 | 88.5 | 983 |
| 850.78 | 87.5 | 1005 |
| 852.2 | 86.5 | 1027 |
| 853.649 | 85.5 | 1050 |
| 855.129 | 84.5 | 1073 |
| 856.64 | 83.5 | 1097 |
| 858.18 | 82.5 | 1121 |
| 859.75 | 81.5 | 1145 |
| 861.34 | 80.5 | 1170 |
| 862.96 | 79.5 | 1195 |
| 864.62 | 78.5 | 1221 |
| 866.3 | 77.5 | 1247 |
| 868.009 | 76.5 | 1274 |
| 869.74 | 75.5 | 1301 |
| 871.508 | 74.5 | 1329 |
| 873.308 | 73.5 | 1357 |
| 875.129 | 72.5 | 1385 |
| 876.98 | 71.5 | 1414 |
| 878.86 | 70.5 | 1444 |
| 880.768 | 69.5 | 1474 |
| 882.71 | 68.5 | 1504 |
| 884.68 | 67.5 | 1535 |
| 886.67 | 66.5 | 1566 |
| 888.69 | 65.5 | 1597 |
| 890.75 | 64.5 | 1629 |
| 892.83 | 63.5 | 1662 |
| 894.968 | 62.5 | 1695 |
| 897.04 | 61.5 | 1728 |
| 899.15 | 60.5 | 1761 |
| 901.3 | 59.5 | 1794 |
| 903.49 | 58.5 | 1829 |
| 905.729 | 57.5 | 1864 |
| 908 | 56.5 | 1899 |
| 910.32 | 55.5 | 1935 |
| 912.68 | 54.5 | 1972 |
| 915.08 | 53.5 | 2010 |
| 917.52 | 52.5 | 2048 |

TABLE I-continued

| Probe Frequency (kHz) | % Water | Count (Pulses/Gate Period) |
|---|---|---|
| 920 | 51.5 | 2087 |
| 922.529 | 50.5 | 2126 |
| 925.089 | 49.5 | 2166 |
| 927.7 | 48.5 | 2207 |
| 930.35 | 47.5 | 2248 |
| 933.04 | 46.5 | 2290 |
| 935.54 | 45.5 | 2329 |
| 938.14 | 44.5 | 2370 |
| 940.729 | 43.5 | 2410 |
| 943.3 | 42.5 | 2451 |
| 945.86 | 41.5 | 2491 |
| 948.4 | 40.5 | 2530 |
| 950.92 | 39.5 | 2570 |
| 953.43 | 38.5 | 2609 |
| 955.92 | 37.5 | 2648 |
| 958.39 | 36.5 | 2686 |
| 960.849 | 35.5 | 2725 |
| 963.288 | 34.5 | 2763 |
| 965.72 | 33.5 | 2801 |
| 968.12 | 32.5 | 2838 |
| 970.508 | 31.5 | 2876 |
| 972.889 | 30.5 | 2913 |
| 975.209 | 29.5 | 2949 |
| 977.558 | 28.5 | 2986 |
| 979.87 | 27.5 | 3022 |
| 982.059 | 26.5 | 3056 |
| 984.249 | 25.5 | 3090 |
| 986.39 | 24.5 | 3124 |
| 988.47 | 23.5 | 3156 |
| 990.508 | 22.5 | 3188 |
| 992.48 | 21.5 | 3219 |
| 994.39 | 20.5 | 3249 |
| 996.246 | 19.5 | 3278 |
| 998.07 | 18.5 | 3306 |
| 999.849 | 17.5 | 3334 |
| 1001.63 | 16.5 | 3362 |
| 1003.31 | 15.5 | 3388 |
| 1004.93 | 14.5 | 3414 |
| 1006.53 | 13.5 | 3439 |
| 1008.12 | 12.5 | 3463 |
| 1009.68 | 11.5 | 3488 |
| 1011.21 | 10.5 | 3512 |
| 1012.69 | 9.5 | 3535 |
| 1014.14 | 8.5 | 3557 |
| 1015.56 | 7.5 | 3580 |
| 1016.53 | 6.5 | 3595 |
| 1018.28 | 5.5 | 3622 |
| 1019.59 | 4.5 | 3643 |
| 1020.86 | 3.5 | 3662 |
| 1022.09 | 2.5 | 3682 |
| 1023.29 | 1.5 | 3700 |
| 1024.45 | .5 | 3719 |

Table I shows that for a two-inch Halliburton capacitance probe, the analog input signal will have the listed frequencies when the respective listed percentages of water are detected in the monitored emulsion. These are known response parameters for this example of the capacitance probe 26 and the preferred embodiment of the present invention. The third column of Table I shows the number of pulses (i.e., cycles of frequency, or periods, of the analog input signal) passed through the NAND gate 56 for the specific gate open period resulting from the specific construction of the clock circuit 38 shown in FIG. 5A (15.625 msec.) The entries in this third column are computed with the following formula (rounded to the whole number): *count (pulses/gate period)* = (*frequency* × 1000 × 0.015625) − (3 × 4096).

Table I lists entries at the one-half percentage points of the watercut because in the preferred embodiment the digital values stored in the digital memory are in whole number increments varying by one and changing at the one-half percentage points. That is, the digital values stored in the PROM 82 in the preferred embodiment are whole number watercut percentages from zero through one hundred percent. A digital value is changed to the next higher or lower whole number percentage at the one-half point between the two numbers. This is shown in Table II:

TABLE II

| PROM 82 Byte (in Decimal) | Digital Value (in Hexadecimal) |
|---|---|
| BYTE 0 to 773 | 9B |
| BYTE 774 to 790 | 9C |
| BYTE 791 to 807 | 9D |
| BYTE 808 to 825 | 9E |
| BYTE 826 to 843 | 9F |
| BYTE 844 to 862 | A0 |
| BYTE 863 to 881 | A1 |
| BYTE 882 to 900 | A2 |
| BYTE 901 to 920 | A3 |
| BYTE 921 to 941 | A4 |
| BYTE 942 to 962 | A5 |
| BYTE 963 to 983 | A6 |
| BYTE 984 to 1005 | A7 |
| BYTE 1006 to 1027 | A8 |
| BYTE 1028 to 1050 | A9 |
| BYTE 1051 to 1073 | AA |
| BYTE 1074 to 1097 | AB |
| BYTE 1098 to 1121 | AC |
| BYTE 1122 to 1145 | AD |
| BYTE 1146 to 1170 | AE |
| BYTE 1171 to 1195 | AF |
| BYTE 1196 to 1221 | B0 |
| BYTE 1222 to 1247 | B1 |
| BYTE 1248 to 1274 | B2 |
| BYTE 1275 to 1301 | B3 |
| BYTE 1302 to 1329 | B4 |
| BYTE 1330 to 1357 | B5 |
| BYTE 1358 to 1385 | B6 |
| BYTE 1386 to 1414 | B7 |
| BYTE 1415 to 1444 | B8 |
| BYTE 1445 to 1474 | B9 |
| BYTE 1475 to 1504 | BA |
| BYTE 1505 to 1535 | BB |
| BYTE 1536 to 1566 | BC |
| BYTE 1567 to 1597 | BD |
| BYTE 1598 to 1629 | BE |
| BYTE 1630 to 1662 | BF |
| BYTE 1663 to 1695 | C0 |
| BYTE 1696 to 1728 | C1 |
| BYTE 1729 to 1761 | C2 |
| BYTE 1762 to 1794 | C3 |
| BYTE 1795 to 1829 | C4 |
| BYTE 1830 to 1864 | C5 |
| BYTE 1865 to 1899 | C6 |
| BYTE 1900 to 1935 | C7 |
| BYTE 1936 to 1972 | C8 |
| BYTE 1973 to 2010 | C9 |
| BYTE 2011 to 2048 | CA |
| BYTE 2049 to 2087 | CB |
| BYTE 2088 to 2126 | CC |
| BYTE 2127 to 2166 | CD |
| BYTE 2167 to 2207 | CE |
| BYTE 2208 to 2248 | CF |
| BYTE 2249 to 2290 | D0 |
| BYTE 2291 to 2329 | D1 |
| BYTE 2330 to 2370 | D2 |
| BYTE 2371 to 2410 | D3 |
| BYTE 2411 to 2451 | D4 |
| BYTE 2452 to 2491 | D5 |
| BYTE 2492 to 2530 | D6 |
| BYTE 2531 to 2570 | D7 |
| BYTE 2571 to 2609 | D8 |
| BYTE 2610 to 2648 | D9 |
| BYTE 2649 to 2686 | DA |
| BYTE 2687 to 2725 | DB |
| BYTE 2726 to 2763 | DC |
| BYTE 2764 to 2801 | DD |
| BYTE 2802 to 2838 | DE |
| BYTE 2839 to 2876 | DF |
| BYTE 2877 to 2913 | E0 |
| BYTE 2914 to 2949 | E1 |
| BYTE 2950 to 2986 | E2 |
| BYTE 2987 to 3022 | E3 |
| BYTE 3023 to 3056 | E4 |
| BYTE 3057 to 3090 | E5 |

TABLE II-continued

| PROM 82 Byte (in Decimal) | Digital Value (in Hexadecimal) |
|---|---|
| BYTE 3091 to 3124 | E6 |
| BYTE 3125 to 3156 | E7 |
| BYTE 3157 to 3188 | E8 |
| BYTE 3189 to 3219 | E9 |
| BYTE 3220 to 3249 | EA |
| BYTE 3250 to 3278 | EB |
| BYTE 3279 to 3306 | EC |
| BYTE 3307 to 3334 | ED |
| BYTE 3335 to 3362 | EE |
| BYTE 3363 to 3388 | EF |
| BYTE 3389 to 3414 | F0 |
| BYTE 3415 to 3439 | F1 |
| BYTE 3440 to 3463 | F2 |
| BYTE 3464 to 3488 | F3 |
| BYTE 3489 to 3512 | F4 |
| BYTE 3513 to 3535 | F5 |
| BYTE 3536 to 3557 | F6 |
| BYTE 3558 to 3580 | F7 |
| BYTE 3581 to 3595 | F8 |
| BYTE 3596 to 3622 | F9 |
| BYTE 3623 to 3643 | FA |
| BYTE 3644 to 3662 | FB |
| BYTE 3663 to 3682 | FC |
| BYTE 3683 to 3700 | FD |
| BYTE 3701 to 3719 | FE |
| BYTE 3720 to 4096 | FF |

By way of example, the first entry in Table II specifies that byte 0 to byte 773 (which byte numbers are in decimal) of the PROM 82 are loaded with the 8-bit digital value 0011011 (identified in Table II by the hexadecimal nomenclature "9B"). This means that the 774 locations in the digital memory having addresses from zero through 773 (in decimal) have the 8-bit byte 10011011 (from most significant to least significant bit) stored thereat. This stored digital value represents a one hundred percent watercut. This corresponds to the first entry in Table I which specifies that for a frequency up to 835.929 kilohertz (kHz) [corresponding to a count from the count circuit 32 of up to 773 (in decimal)] the linearization implemented by this specific embodiment specifies that such monitored watercut is to be represented as one hundred percent. For a frequency between 835.929 kHz and 837.008 kHz (which frequency range actually designates a watercut range of 99.5%-98.5%), the watercut will be represented as 99% as indicated in Table I. From Table II, this corresponds to loading in locations 774 through 790 (in decimal) of the PROM 82 the digital value 0011100 ("9C" in hexadecimal). The remainders of Tables I and II are similarly related.

From the foregoing example, it is apparent that the nonlinear frequency changes are converted into digital values which change linearly from watercut percentage to watercut percentage. In the described example the digital values are changed by adding one to the preceding value [e.g., the second digital value entered in Table II, representing 99% watercut, is "9C" which equals "9B" (the first entry, representing 100% watercut)+1].

Referring to FIG. 5B, an output of a digital value from the digital memory is latched into the latch circuit 36 in response to the latch control signal from the circuit 38. The latch circuit 36 is implemented by an integrated circuit latch 86 shown in FIG. 5B. This integrated circuit is an octal flip-flop in the preferred embodiment. It is used to temporarily store the digital value output from the PROM 82 in the preferred embodiment. This holds the digital value for communication to the analog output means defined by the circuits 40, 42 of the upper printed circuit board 22. The integrated circuit 86 has latch data inputs connected to the outputs 84 from the PROM 82 as is apparent from FIG. 5B. The latch 86 also has latch data outputs to which the temporarily stored digital value is provided, which outputs are connected to the terminal 50 for connection to the driver and opto-isolator circuit 40 on the printed circuit board 22. A clock input of the integrated circuit 86 is connected to the conductor 70 over which the latch control signal is provided.

Figure 6A:
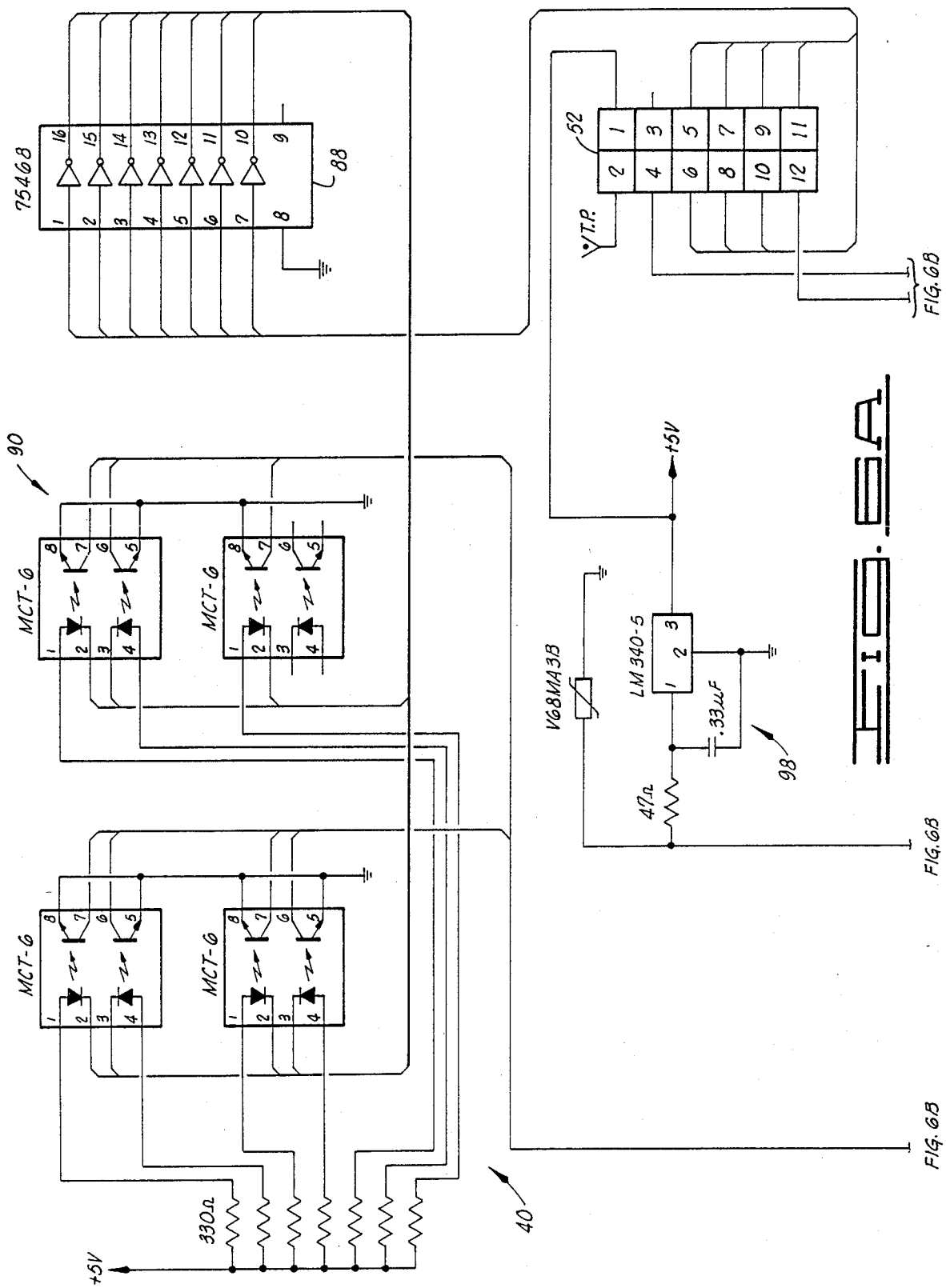

The driver and opto-isolator circuit 40, which forms another part of the means for communicating a digital value from the data outputs of the digital memory, isolates the analog output means from the earth ground associated with the digital circuitry. This earth ground results from the connection of the digital circuitry to the capacitance probe which generally will have one of its metallic components connected to earth ground. This isolation allows the analog output circuit to provide a floating output. As shown in FIG. 6A, the preferred embodiment of this part of the invention includes an integrated circuit driver chip 88 having inputs connected to the terminal 52 receiving the outputs from the latch circuit 36. The outputs of the driver chip 88 are connected to respective inputs of optical coupling devices 90 for optically coupling the digital values to the digital-to-analog converter circuit 42.

The digital-to-analog converter circuit 42 of the preferred embodiment is the same type as used in the Halliburton Services Net Oil Analyzer, but configured to provide a 4-20 milliampere (mA) current output. In the preferred embodiment the 4-20 mA magnitude represents, in linear fashion, the full-scale 0 to 100% watercut defined by the digital values stored in the PROM 82. It is contemplated, however, that any other suitable type of analog output can be used to give a linear representation of the watercut. The digital-to-analog converter functions in a known manner to convert the optically coupled digital value into an analog signal to define the analog output signal which is provided to a terminal 92.

The terminal 92 also has inputs for receiving a power input. The terminal 92 is also used to communicate the analog input signal, in the form in which it is provided at the output of the oscillator circuit 24, to equipment external to the watercut monitor device 8 of the present invention.

FIGS. 7 and 8 show two power supply configurations by which the present invention can be energized.

For the present invention to provide a floating analog output as described hereinabove, two isolated power supplies must be used. This configuration is illustrated in FIG. 7. In this configuration, a power supply 94 powers the analog circuitry shown in FIG. 6 to provide the analog output signal. The connections for this power supply are shown in FIG. 7. The digital circuitry is energized by a power supply 96 which is connected to the power inputs of the terminal 92. These inputs connect the power supply 96 to a power regulator circuit 98 shown in FIG. 6A. In the preferred embodiment the power supply 96 should have an output of 12-30 volts and a current capacity of 200 mA. The power supply 94 needs an output of 24-48 volts depending on the load as indicated in the following table.

| Supply 94 Voltage | Maximum Load |
|---|---|
| 24V | 450 ohms |
| 28V | 600 ohms |
| 32V | 700 ohms |

-continued

| Supply 94 Voltage | Maximum Load |
|---|---|
| 40V | 800 ohms |
| 48V | 1000 ohms |

If a floating analog output is not needed, the present invention can be operated by a single power supply. This is illustrated in FIG. 8. A single power supply 100 is connected as shown in FIG. 8. The power supply 100 needs an output of 24-30 volts and a current capacity of 200 mA. The specific voltage required depends on the load driven the same as for the power supply 94; therefore, the entries in the foregoing table set forth with reference to the power supply 94 are pertinent to the power supply 100.

To use the watercut monitor device 2 of the present invention, it first is calibrated. It is generally necessary to adjust the capacitance probe output on each installation. This involves filling the probe 26 with a sample of clean, dry crude oil from the location to be served and observing the output frequency. This adjustment may be made with the probe removed from the flowline. For proper calibration, the probe must be completely liquid-filled.

Once the watercut monitor device 8 has been connected to the host equipment and filled with oil, the frequency generated by the probe is monitored. This can be by connecting a frequency counter to the analog output signal outputs of the terminal 92. If the probe frequency is not correct (e.g., between 1024.9 and 1025.1 kilohertz in the preferred embodiment), the probe must be adjusted by unscrewing a pipe plug from a trimmer capacitor access hole in the support body 14 and by adjusting a trimmer capacitor on the probe circuit assembly until the output is within this range. This is the only adjustment required to calibrate the capacitance probe, and it is an adjustment known to the art.

If adjustment of the digital-to-analog conversion circuit 42 is needed, a potentiometer 102 shown in FIG. 6B is adjusted until the analog output is 4 mA (indicating 0% watercut). With the probe signal outputs of the terminal 92 shorted together, a potentiometer 104 is then adjusted until the analog output is 20 mA (indicating 100% watercut). After this is done, the short of the probe signal outputs is removed and the frequency from the analog output pins is again checked to make sure it returns to 4 mA. The probe signal outputs are also checked to make sure the frequency returns to the proper range (e.g., 1025 kilohertz±0.1 kilohertz). If not, the foregoing procedure is repeated as needed.

If the clock circuit 38 needs to be adjusted, a trimmer-capacitor 106 shown in FIG. 5A is adjusted. The crystal frequency may be monitored from pin 9 of the chip 60 as connected through the terminal member 50 to the water-terminal member (see test point "TP" in FIG. 6A). In the preferred embodiment, the trimmer capacitor 106 should be adjusted until the frequency out of the oscillator is 32,768 hertz. Once the device has been calibrated, it is ready for use in providing a linearized analog signal proportional to the watercut of the monitored emulsion. The sine wave signal generated in the preferred embodiment at the output of the oscillator circuit 24 has a frequency which varies nonlinearly with the watercut of the emulsion around the probe 6. The signal conditioning circuit 28 amplifies and shapes the analog signal and feeds it into the gating circuit 30. As has been described, the gating circuitry is open for a fixed, predetermined duration in response to the gate control signal generated by the crystal controlled oscillator and associated divider and control circuitry 38. Because the frequency of the analog input sine wave from the capacitance probe oscillator varies with the watercut, the number of pulses captured during a gate open period is dependent upon the watercut of the emulsion sensed by the probe at that time. Because the gate opening is of a fixed duration and the frequency out of the probe oscillator is known and repeatable data, there is a definite but non-linear relationship between the watercut of the emulsion sensed by the probe and the number of pulses received during a gate open period.

When the gate is open, the high frequency sine wave from the analog input circuitry is fed into the binary counters 78, 80. The outputs of these counters are fed into the address lines of the PROM 82. This selects the linearized digital value stored at that addressed location. This linearized digital value is fed to the latch 86 which temporarily holds the value for use by the analog output circuitry shown in FIGS. 6A and 6B. In the preferred embodiment the control lines of the PROM 82 are set such that the PROM outputs are always enabled, thereby necessitating the use of the latch 86 to hold only a single retrieved digital value.

At the end of a gate open period, the gate closes. After the gate has closed, the crystal controlled oscillator circuitry 38 pulses the clock line of the latch 86. This latches the latest PROM output data onto the latch outputs. This latching is necessary due to the fact that during the gate open period, the outputs of the PROM are changing since it is always enabled. After the crystal controlled oscillator circuitry 38 has pulsed the latch 86, it pulses the reset lines of the counters 78, 80 to reset the counter outputs to zero in time for the next gate open period.

The outputs of the latch 86 are connected through the terminal 50 to the drivers 88 and the opto-isolators 90 which electrically isolate, but communicate the value of the digital outputs from the latch 86 to the digital-to-analog circuitry 42. These opto-isolators electrically isolate the analog outputs from the digital circuitry which, due to the nature of the probe design, is almost always connected to earth ground. It is often undesirable to have the equipment to which the analog output is connected tied to earth ground as would be the case were it not for the opto-isolators 90. The outputs from the opto-isolators 90 are taken by the digital-to-analog converter 42 and converted into the analog output signal maintaining the linearization relative to the detected watercut. This analog output signal is communicated through the appropriate outputs of the terminal 92 for interfacing to the desired data collection device.

In summary of the present invention and particularly the preferred embodiment described herein, the watercut monitor device 8 of the present invention is a solid state electronic instrument which determines the percent watercut in an oil emulsion without requiring the physical separation of the fluids. A capacitance probe technique is employed so that the emulsion stream can be continuously surveyed. The frequency generated in response to the capacitance probe is non-linearly related to the watercut of the emulsion stream in the probe. The watercut monitor device 8 compensates for the non-linear relationship between frequency and watercut by strictly digital techniques. In response to this digital linearization, an analog output signal which varies linearly with watercut is provided. In the preferred embodiment this linearization is indicated by a 4–20 milliampere current signal. In the preferred embodiment this current signal may be completedly floating if two external power supplies are used; however, operation with a single power supply is also possible except that the capability of providing a floating output is not present in that case.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for providing an analog output signal which is linearly proportional to the percentage of water in an emulsion, said apparatus comprising:
    analog input means for generating an analog input signal non-linearly proportional to the percentage of water in the emulsion;
    digital means, responsive to said analog input means, for digitizing said analog input signal and for translating the digitized analog input signal into a digital signal linearly proportional to the percentage of water in the emulsion, said digital means including:
        first conversion means, connected to said analog input means, for periodically converting said analog input signal into a respective digital count; and
        second conversion means, connected to said first conversion means, for converting each said respective digital count into a respective digital value defining said digital signal; and
    analog output means, responsive to said digital means, for converting said digital signal into an analog output signal so that said analog output signal is also linearly proportional to the percentage of water in the emulsion.

2. An apparatus as defined in claim 1, wherein said first conversion means includes:
    clock means for providing a gate control signal, a counter reset signal and a latch control signal;
    a digital counter responsive to said counter reset signal; and
    gate means, connected to said analog input means, to said clock means and to said digital counter, for passing or blocking said analog input signal to or from said digital counter in response to the state of said gate control signal.

3. An apparatus as defined in claim 2, wherein said second conversion means includes:
    digital memory means, connected to said digital counter, for storing each said respective digital value at a location having an address corresponding to the respective one of said digital count; and
    latch means, connected to said digital memory means, for storing, in response to said latch control signal, a digital value output from said digital memory means so that the digital value stored by said latch means defines said digital signal.

4. An apparatus as defined in claim 3, wherein said digital memory means includes a programmable read only memory comprising:
    memory storage locations at which said digital values are stored;
    address inputs connected to said digital counter so that a digital count from said digital counter selects a respective memory storage location to retrieve the digital value stored thereat; and
    data outputs to which a retrieved digital value is provided for communication to said latch means to which said data outputs are connected.

5. An apparatus as defined in claim 3, wherein said analog output means includes digital-to-analog converter means for converting the digital value stored in said latch means into an analog signal defining said analog output signal.

6. An apparatus for providing an analog output signal which is linearly proportional to the percentage of water in an emulsion, said apparatus comprising:
    analog input means for generating an analog input signal non-linearly proportional to the percentage of water in the emulsion;
    digital means, responsive to said analog input means, for digitizing said analog input signal and for translating the digitized analog input signal into a digital signal linearly proportional to the percentage of water in the emulsion;
    analog output means, responsive to said digital means, for converting said digital signal into an analog output signal so that said analog output signal is also linearly proportional to the percentage of water in the emulsion; and
    wherein said digital means includes a programmable read only memory comprising:
        memory storage locations at which are stored digital values linearly proportional to the percentage of water in the emulsion;
        address inputs connected to receive the digitized analog input signal so that the received digitized analog input signal selects a respective memory storage location to retrieve the digital value stored thereat; and
        data outputs to which a retrieved digital value is provided for communication therefrom to said analog output means.

7. An apparatus for providing an analog output signal which is linearly proportional to the percentage of water in an emulsion, said apparatus comprising:
    analog input means for generating an analog input signal non-linearly proportional to the percentage of water in the emulsion, said analog input signal having a frequency non-linearly proportional to the percentage of water in the emulsion;
    digital means, responsive to said analog input means, for digitizing said analog input signal and for translating the digitized analog input signal into a digital signal linearly proportional to the percentage of water in the emulsion, said digital means including:
        counter means for defining a digital count corresponding to the number of cycles of the frequency of said analog input signal received by said counter means; and
        digital memory means for storing digital values at addressable locations so that in response to said digital memory means receiving a digital count from said counter means, the respective digital value stored at the location addressed by the received digital count is output from said digital memory means for defining said digital signal which is linearly proportional to the percentage of water in the emulsion; and analog output means, responsive to said digital means, for converting said digital signal into an analog output signal so that said analog output signal is also linearly proportional to the percentage of water in the emulsion.

8. An apparatus as defined in claim 7, wherein said analog output means includes digital-to-analog converter means for converting the digital value output from said digital memory means into an electrical current having a magnitude representing the percentage of water in the emulsion, said electrical current defining said analog output signal.

9. A self-contained watercut monitor apparatus for providing an analog output signal which is linearly proportional to the percentage of water in the mixture, said apparatus comprising:

analog input means, responsive solely to a capacitance which is variable with variations in the percentage of water in the mixture, for generating an analog input signal non-linearly proportional to the percentage of water in the mixture;

digital means, responsive solely to said analog input means and including a digital memory, for digitizing said analog input signal and for translating the digitized analog input signal through said digital memory into a digital signal linearly proportional to the percentage of water in the mixture; and analog output means, responsive to said digital means, for converting said digital signal into an analog output signal so that said analog output signal is also linearly proportional to the percentage of water in the mixture.

10. An apparatus as defined in claim 9, wherein:
said apparatus further comprises a support body;
said analog input means includes:
a capacitance probe mounted in said support body and having an electrical capacitance which is variable in response to changes in the percentage of water in the emulsion in said support body; and
circuit means, connected to said capacitance probe, for providing said analog input signal so that said analog input signal has a characteristic determined in response to said electrical capacitance of said capacitance probe; and
said support body includes a housing in which said circuit means, said digital means, and said analog output means are disposed.

11. An apparatus as defined in claim 10, wherein:
said circuit means and said digital means include a single common printed circuit board mounted in said housing and connected to said capacitance probe; and
said analog output means includes a single printed circuit board mounted in said housing above, and connected to, said printed circuit board of said circuit means and said digital means.

12. A watercut monitor device, comprising:
capacitance means for providing an electrical capacitance which varies in response to the water content of an oil and water emulsion;
oscillator means, connected to said capacitance means, for generating an oscillating signal having a frequency determined in response to said electrical capacitance;
timing means for providing a timing signal having a first state and a second state;
gate means, connected to said oscillator means and said timing means, for communicating the number of cycles of frequency of said oscillating signal in response to the first state of said timing signal and for not communicating the number of cycles of frequency of said oscillating signal in response to the second state of said timing signal;
count means, connected to said gate means for generating a digital count of the cycles of frequency of said oscillating signal communicated through said gate means;
digital memory means for storing digital values, each of said digital values designates water content of an oil and water emulsion and each of said digital values corresponds to a digital count of said count means, said digital memory means including:
address input means for receiving said digital count from said count means so that the received digital count defines a memory location address;
a plurality of digital storage locations, each of said locations being accessible in response to a respective memory location address and each of said locations containing one of said digital values; and
data output means for communicating the digital value stored at the digital storage location addressed by the memory location address defined by the received digital count;
digital-to-analog converter means for converting a digital value from said digital memory means into an analog output signal having a characteristic linearly proportional to the designated water content of an oil and water emulsion; and
means for communicating a digital value from said data output means to said digital-to-analog converter means.

13. A device as defined in claim 12, further comprising means, connected between said oscillator means and said gate means, for interfacing said oscillating signal to said gate means.

14. A device as defined in claim 12, wherein said gate means includes a logic circuit comprising an input connected to said oscillator means, an input connected to said timing means, and an output connected to said count means.

15. A device as defined in claim 12, further comprising:
a first output terminal connected to said digital-to-analog converter means so that said analog output signal is provided to said first output terminal; and
a second output terminal connected to said oscillator means so that said oscillating signal is provided to said second output terminal.

16. A device as defined in claim 12, wherein:
said means for communicating a digital value from said data output means to said digital-to-analog converter means includes:
latch means for temporarily storing a digital value communicated through said data output means, said latch means including:
latch data inputs connected to said data output means;
latch data outputs to which the temporarily stored digital value is provided; and
a clock input; and
means for coupling the digital value from said latch data outputs to said digital-to-analog converter means; and said timing means includes means for providing, during a second state of said timing signal, a latch control signal to said clock input of said latch means, and said timing means further includes means for providing, after said latch control signal and before the next first state of said timing signal, a reset signal to said count means.

17. A device as defined in claim 16, wherein said means for coupling the digital value from said latch data outputs to said digital-to-analog converter means includes means for optically coupling the digital value to, but for electrically isolating said latch means from, said digital-to-analog converter means.

18. A method of providing a linearized analog signal proportional to the watercut of an emulsion, comprising the
   (a) generating a cyclic electrical signal having its cyclic period non-linearly responsive to the watercut;
   (b) counting the number of cyclic periods of the electrical signal occurring during a predetermined time;
   (c) communicating the count obtained in said step (b) to address lines of an integrated circuit digital memory including memory locations at which digital values are stored, each digital value defining a linearization of a count of the number of cyclic periods of the electrical signal;
   (d) outputting from the digital memory, in response to said step (c), the digital value stored at the memory location addressed by the communicated count; and
   (e) converting the digital value output in said step (d) into an analog signal having a detectable characteristic representing the linearization defined by the output digital value.

19. A method as defined in claim 18, wherein said step (a) includes:
   flowing an emulsion from an outlet of a separator through a capacitance probe so that the electrical capacitance of the probe is proportional to the watercut of the emulsion, which separator includes an inlet into which flows a production stream from an oil-producing well; and
   activating an electrical oscillator circuit in response to the capacitance of the capacitance probe so that the cyclic electrical signal is provided at an output of the oscillator circuit.

20. A method as defined in claim 18, wherein said step (e) includes:
   temporarily storing the digital value output from the digital memory in a digital latch; and
   optically coupling the output from the digital latch to an analog-to-digital converter circuit having an output through which the analog signal is provided.

* * * * *